United States Patent [19]

Porter

[11] Patent Number: 5,567,415
[45] Date of Patent: Oct. 22, 1996

[54] ULTRASOUND CONTRAST AGENTS AND METHODS FOR THEIR MANUFACTURE AND USE

[75] Inventor: Thomas R. Porter, Omaha, Nebr.

[73] Assignee: The Board of Regents of the University of Nebraska, Lincoln, Nebr.

[21] Appl. No.: 252,286

[22] Filed: Jun. 1, 1994

Related U.S. Application Data

[63] Continuation-in-part of Ser. No. 113,415, Aug. 27, 1993, abandoned, which is a continuation-in-part of Ser. No. 57,298, May 14, 1993, abandoned, which is a continuation-in-part of Ser. No. 60,751, May 12, 1993.

[51] Int. Cl.⁶ ..................................................... A61K 49/00
[52] U.S. Cl. ..................................... 424/9.52; 128/662.02
[58] Field of Search ....................... 424/9.52; 128/662.02

[56] References Cited

U.S. PATENT DOCUMENTS 5,413,774  5/1995  Schneider et al. ..................... 424/9.51

FOREIGN PATENT DOCUMENTS 9205806  4/1992  WIPO .

*Primary Examiner*—José G. Dees
*Assistant Examiner*—Mary C. Cebulak
*Attorney, Agent, or Firm*—Zarley, McKee, Thomte, Voorhees, & Sease

[57] ABSTRACT

This invention relates to a new ultrasound contrast agent of the type which relies on microbubbles for echogenicity. The improvement comprises enhancing the internal atmosphere of the microbubbles with an amount of perfluoropropane which is effective for visually detecting myocardial uptake upon echocardiogram following peripheral intravenous injection of said agent into a host. The contrast agent of this invention is unique in that it makes possible the non-invasive visual detection of myocardial uptake. In addition, the contrast agent of this invention makes feasible safe and consistent, non-invasive methods for visually assessing, qualitatively or quantitatively, not only myocardial perfusion, but renal and hepatic perfusion, and for detecting severity of coronary arterial stenosis. the invnetion also relates to a method of ultrasonic imaging for use in medical procedures, comprising the steps of injecting perfluoropropane-containing microbubbles into a mammal to thereby alter the acoustic properties of a predetermined area, and ultrasonically scanning an area including said predetermined area so as to obtain an image of said predetermined area.

8 Claims, No Drawings

ULTRASOUND CONTRAST AGENTS AND METHODS FOR THEIR MANUFACTURE AND USE

FIELD OF THE INVENTION

This application is a continuation-in-part application of U.S. patent application Ser. No. 08/113,415, abandoned for A METHOD AND COMPOSITION FOR OPTIMIZING VIDEOINTENSITY IN ULTRASONIC IMAGING AND ECHOCARDIOGRPAHY, filed by Thomas R. Porter on Aug. 27, 1993, which is a continuation-in-part application of U.S. patent application Ser. No. 08/057,298, abandoned for A METHOD AND COMPOSITION FOR OPTIMIZING VIDEOINTENSITY IN ULTRASONIC IMAGING AND ECHOCARDIOGRAPHY, filed by Thomas R. Porter on May 14, 1993, which is a continuation-in-part application of U.S. patent application Ser. No. 08/060,751 for A METHOD AND COMPOSITION FOR OPTIMIZING LEFT VENTRICULAR VIDEOINTENSITY IN ECHOCARDIOGRAPHY, filed by Thomas R. Porter on May 12, 1993. All of said applications are commonly owned.

This invention relates to a new and improved ultrasonic contrast agent and to its manufacture and use in ultrasonic imaging and echocardiography. More particularly, the contrast agent of this invention relates to the sonicated microbubble type, but is unique in that it makes possible the non-invasive visual detection of myocardial uptake, as discussed more fully hereinafter. In addition, the contrast agent of this invention makes feasible safe and consistent, non-invasive methods for visually assessing, qualitatively or quantitatively, not only myocardial perfusion, but renal and hepatic perfusion, and for detecting severity of coronary arterial stenosis.

BACKGROUND OF THE INVENTION

Ultrasonic imaging is used as a diagnostic tool to aid in therapeutic procedures. Ultrasonic energy is produced by generating and receiving sound waves with an ultrasonic scanner. Contrast agents which are echogenic are preferentially used to create ultrasonic energy in an area of interest. In ultrasound imaging, videotape images obtained following contrast injection are digitized, allowing the gray scale to be quantified from 1 to 225 gray scale units for 30 cardiac cycles. The contrast intensity is plotted on the vertical axis against time on the horizontal axis. The peak videointensity (corrected for baseline intensity) is determined as the highest point on the time intensity curve. For a discussion of contrast echographic instrumentation, see, for example, De Jong N, "Acoustic properties of ultrasound contrast agents", CIP-GEGEVENS KONINKLIJKE BIBLIOTHEEK, DEN HAAG (1993), pages 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

A multiplicity of potential ultrasonic imaging agents has been reported for contrast echocardiography. It is believed that no such agent routinely attains visually discernible myocardial uptake following peripheral intravenous injection. Although there have been many reports of transpulmonary transmission of ultrasound contrast agents following intravenous injection and despite the fact that myocardial opacification on echocardiogram can be produced by left sided injection of such contrast agents, visualization of myocardial contrast has not been achieved by intravenous administration of sonicated microbubbles.

Most recently, sonicated albumin and sonicated dextrose/albumin have been shown to produce variable degrees of left ventricular chamber ultrasound contrast following intravenous injection. (See Villanueva et al. Circulation 85:1557–1564, 1992; Lin et al. Int J Card Imaging 8:53–6, 1992; Feinstein et al. J Am Coll Cardiol 16:316–224, 1990; Keller et al. Am Heart J 114:570–575, 1987; and Shapiro et al. J Am Coll Cardiol 16:1603–1607, 1990). The microbubbles of these contrast agents are small (4–6 microns) and are capable of swift transpulmonary passage. However, visually discernible myocardial uptake of such microbubbles following peripheral intravenous injection has not been possible because of the rapid diffusion of blood soluble oxygen and nitrogen inside the microbubble into the blood which consequently loses its ultrasound reflective properties (e.g., see Porter et al. J Am Soc Echocard Supplement 7:S1, May 1994, and Weyman AE: Principles and Practice of Echocardiography, Malvern, Pa.: Lea & Febiger, 1994; pp.302–26.)

An important objective of this invention is to provide a contrast agent and methods for its production and use wherein microbubble survival and subsequent myocardial ultrasound contrast is improved sufficiently to make possible visually discernible myocardial uptake of such microbubbles following non-invasive peripheral intravenous injection. This and other objectives of this invention will become apparent in the following discussion.

SUMMARY OF THE INVENTION

In accordance with this invention, there is provided an improved ultrasound contrast agent which relies on microbubbles for echogenicity, in which the improvement comprises enhancing the internal atmosphere of the microbubbles with an amount of perfluoropropane which is effective for visually detecting myocardial uptake upon echocardiogram following peripheral intravenous injection of said agent into a host. The perfluoropropane gas content of the microbubbles is sufficient to lower microbubble gas solubility and diffusivity in vivo in blood. Generally, the minimum amount of perfluoropropane gas in the microbubbles which is effective is that amount which results in microbubbles which pass reliably through the pulmonary circulation without collapse. This is evidenced by opacification of the myocardium of the left ventricle of the heart following intravenous injection and can be visually discerned by echocardiography, for example, in accordance with standard methods or the methods described more fully hereinafter.

Consequently, the invention also provides a method of ultrasonic imaging for use in medical procedures, comprising the steps of injecting the unique perfluoropropane-containing microbubbles of this invention into a host to thereby alter the acoustic properties of a predetermined area, and ultrasonically scanning an area including said predetermined area so as to obtain an image of said predetermined area.

Other pharmaceutically acceptable inert gases, such as sulfur hexafluoride, can be used, provided such gases have a diffusion coefficient and blood solubility lower than nitrogen or oxygen, the components of room air. Perfluoropropane ($C_3F_8$) is especially preferred because of its demonstrated safety for intraocular injection in humans. Perfluoropropane has been used in human studies for intraocular injections to stabilize retinal detachments (Wong and Thompson, Ophthalmology 95:609–613) and is useful in treating complicated retinal detachments by providing internal tamponade of retinal breaks. Treatment with intraocular perfluoropropane is considered to be the standard of care for treatment of this disorder. However, it should be apparent to one of ordinary skill in the art that other inert gases with a similar or lower blood solubility to perfluoropropane can be used, provided that they are pharmaceutically acceptable.

Although intravenous echo contrast agents made from sonicated microbubbles are known (e.g., ALBUNEX, Molecular Biosystems, Inc.) and can be employed in this invention, it is preferred to use a sonicated aqueous solution containing a mixture of a pharmaceutically acceptable saccharide, e.g., dextrose, and a protein, e.g., albumin. Generally, sonication is performed in an air atmosphere. In an especially preferred embodiment, dextrose, which is readily available in pharmaceutically acceptable dosage forms, is the preferred saccharide and human serum albumin is the preferred protein. Exemplary of other saccharide solutions of this invention are an aqueous monosaccharide solution (e.g. having the formula $C_6H_6O_{12}$, such as, the hexoses, dextrose or fructose, or mixtures thereof), aqueous disaccharide solution (e.g., having the formula $C_{12}H_{22}O_{11}$, such as sucrose, lactose or maltose, or mixtures thereof), or aqueous polysaccharide solution (e.g., soluble starches having the formula $(C_6H_{10}O_5)_n$, wherein n is a whole integer between about 20 and about 200, such as amylose or dextran, or mixtures thereof.

In addition to myocardial imaging the contrast agents of this invention are useful for renal and hepatic imaging. Thus, another embodiment of this invention provides a method for myocardial, renal or hepatic opacification. The method preferred involves obtaining an echo contrast agent of this invention, introducing said echo contrast agent into a host by intravenous injection, and performing an echo contrast study on said host using a suitable Doppler or ultrasound echo apparatus as discussed more fully hereinafter.

The method of ultrasonic imaging in which microbubbles formed by sonicating an aqueous protein solution are injected into a mammal to alter the acoustic properties of a predetermined area which is then ultrasonically scanned to obtain an image of the area for use in medical procedures is well known (e.g., see U.S. Pat. No. 4,572,203, U.S. Pat. No. 4,718,433 and U.S. Pat. No. 4,774,958, the contents of each of which are incorporated herein by reference). It is the use of the unique, stabilized perfluoropropane-containing microbubbles of this invention which constitutes a novel improvement. Thus, in accordance with another embodiment of this invention, there is provided a method of ultrasonic imaging for use in medical procedures comprising the steps of forming an aqueous protein solution (e.g., aqueous dextrose albumin), subjecting said solution to high frequency sonication while exposed to perfluoropropane gas, said sonication forming stabilized microbubbles of relatively uniform size, containing said perfluropropane, and capable of transpulmonary passage, and using the stabilized microbubbles as an injectable contrast agent for said ultrasonic imaging.

DETAILED DESCRIPTION OF THE INVENTION

Sonicated albumin has been used to study coronary flow reserve and immediate post-angioplasty anterograde blood flow reserve in humans. In humans without significant coronary artery disease, left main coronary artery injections of sonicated albumin before and after intracoronary papaverine result in time intensity curves which can be utilized to determine coronary flow reserve. It has been demonstrated that the washout of ultrasound contrast from the human myocardium in this setting correlates with coronary flow reserve measured by more invasive techniques.

Secondly, intracoronary sonicated albumin injections in humans with coronary artery disease, before and after angioplasty, has been done. The functional reserve of the myocardium supplied by the vessel undergoing angioplasty is immediately improved following angioplasty. The degree of improvement depends not on how visually successful the angioplasty was, but on how quantitatively successful the improvement in stenosis area was after angioplasty. Sonicated albumin does not reliably cross the pulmonary circulation into the left ventricular chamber following an intravenous injection, and thus at present cannot be used to non-invasively detect myocardial blood flow.

It has been observed that a microbubble radius decreases as a function of time in a still liquid due to a diffusion gradient present between the internal and external gases of the microbubble. An increase in microbubble size has a significant effect on the persistence of a microbubble within blood. The mean microbubble size of sonicated dextrose albumin ranges from between about 5 to about 6 microns. Since this size is ideal for transpulmonary passage, the major reason for the significant loss in left ventricular and myocardial videointensity produced following intravenous injection is due to the significant diffusion of gases within the microbubble following intravenous injection during transit to the left ventricular cavity. Sonicated dextrose albumin enhanced with an inert gas such as perfluoropropane, having a lower blood solubility than air, produces a significantly higher left ventricular and myocardial videointensity than sonicated albumin alone.

Because of high surface tension, the concentration of nitrogen and oxygen gas within the microbubble is much higher than that in blood, and thus there is a rapid diffusion of this gas into the blood stream following intravenous injection. Wible et al. (Circulation, 88:I-401, 1993) have demonstrated that this diffusion process can be accelerated if one decreased the partial pressure of nitrogen within the blood stream by decreasing the inhaled fraction of nitrogen. This lower external concentration of nitrogen results in loss of the left ventricular videointensity produced by the same intravenous injection of sonicated albumin while inhaling room air. It has also been observed that oxygen rapidly diffuses out of gas bubbles into human blood (See Yang et al., J Biomech 3:275, 1971).

Both nitrogen and oxygen diffuse rapidly across these concentration gradients, but nitrogen appears to dissolve more slowly than oxygen into blood. Since nitrogen is the major component of air, decreasing the concentration gradient for nitrogen across the microbubble improves left ventricular and myocardial videointensity following intravenous injection. Exposing the microbubbles to a non-toxic gas having a lower blood solubility and/or microbubble diffusivity than that of nitrogen and having a gas density of greater than about 0.300 lb/ft$^3$ during sonication increases the size and stability of the microbubbles in sonicated dextrose albumin, while lowering the solubility and diffusivity of the microbubbles in blood.

The contrast agent of this invention, a perfluoropropane-enhanced sonicated dextrose albumin solution is comprised of a sonicated three-fold dilution of 5% human serum albumin with 5% dextrose. During sonication, said solution is perfused with perfluoropropane for about 80 seconds, which lowers the solubility and diffusivity of the microbubble gas. The resulting microbubbles are concentrated at room temperature for at least about 120±5 minutes, wherein the excess solution settles in the sonicating syringe. The excess solution is expelled and the concentrated microbubbles are transferred to a sterile syringe and injected intravenously into a mammal.

Using perfluoropropane to enhance the sonicated contrast agent of this invention will result in a higher degree of myocardial opacification, endocardial border delineation, and enhanced detection of left-sided ultrasound Doppler signals, upon peripheral venous administration. Additionally, using perfluoropropane during sonication creates a more stable microbubble concentration, which subsequently enables ultrasonic visualization of the liver and kidneys following an intravenous injection.

The following examples demonstrate the effect of inert gases on microbubble stability and diffusibility, and the effect of perfluoropropane-enhanced sonicated dextrose albumin on myocardial uptake and videointensity as well as on ultrasonic determination of renal perfusion. In all the following examples all parts and percentages are by weight, unless stated otherwise. All dilutions are by volume.

Preparation of Contrast Agents

Albumin (human) USP, 5% solution (hereinafter referred to as "albumin") and dextrose USP, 5% solution (hereinafter referred to as "dextrose") are obtained from a commercial source. The sonicating system used for sonication is a Heat Systems Ultrasonic Processor Model XL2020 (Heat Systems Inc., Farmingdale, N.Y.). The ½ inch horn transducer is a resonating piezoelectric device. The ½ inch sonicating horn tip is sterilized prior to each sonication.

Sonication of Samples

Sixteen milliliter aliquots of albumin diluted 1:3 with dextrose are drawn up into a 35 cc "Monoject" syringe (Becton Dickinson and Company, Rutherford, N.J.) and sonicated for 80±1 seconds. The "Leur-Lok" of the 35 milliliter syringe is then attached to a stopcock. After mixing the dextrose albumin solution by hand for about 7 to about 10 seconds, the plunger is removed from the top of the syringe. The sterile sonicating horn is then lowered into the open end of the syringe until at the surface of the albumin-dextrose solution. The solution is placed at the horn tip and manually held at this position while continuously sonicating at a frequency of 20,000 Hz and a power output of 210 W for 80±1 seconds to form a stable microbubble solution.

Gas Perfusion of Samples

During sonication, the dextrose albumin mixture is exposed to perfluoropropane gas (Commercial Grade, 99.9% by weight). The gas is drawn up into a sterile syringe through a 0.22 µM filter (Micron Separations Inc., Westborough, Mass.) to prevent contamination. During sonication, 5 milliliters of perfluoropropane gas is manually injected into the solution, over the 80 second time interval, through the stopcock so that the microbubbles produced contain this less soluble gas. The total volume of perfluoropropane-enhanced sonicated dextrose albumin produced with this formulation is 25±2 milliliters. These samples are then used for intravenous injection.

Microbubble Analysis

Microbubble size and purity is determined using hemocytometry. Microscopic inspection of the microbubbles is performed to determine if any coalescent microbubbles are present in the solution. Microbubble concentration is determined using a Coulter Counter. The contrast agent is rejected for use if any of the following conditions are present: the mean microbubble size is 4.0 to 6.0 microns; coalesced microbubbles or strands are detected by light microscopy; or the mean microbubble concentration is $<0.8 \times 10^9$ or $>1.5 \times 10^9$ microbubble/milliliter. The sample is also rejected if the number of microbubbles greater than 10 microns in the sample is greater than 4%.

All samples are stored in 35 milliliter syringes until time of injection. All solutions are given within 36 hours of production. All samples are prepared in a laminar flow hood.

Preparation of Open-Chest Dogs

Mongrel dogs of either sex (15–30 kilograms) are anesthetized with sodium pentobarbital (30 milligram per kilogram intravenously), intubated, and ventilated initially with room air using a positive pressure respirator. A left thoracotomy is performed under sterile conditions and the pericardium incised. In addition to a 19 gauge peripheral intravenous line, eight French catheters are placed in the femoral artery and vein for intravenous administration of ultrasound contrast agents and pressure monitoring. Through one femoral venous sheath, a 7F balloon-tipped thermodilution catheter is placed in the pulmonary artery using fluoroscopy for determination of pulmonary artery pressure and cardiac output. A 7F pigtail catheter is introduced into the left ventricle for pressure measurements (left ventricular systolic and end-diastolic pressure) following injection of each ultrasound contrast agent.

Following adequate surgical exposure, a 3.5 Megahertz ultrasound transducer connected to a commercially available ultrasound scanner (Hewlett Packard Company; Andover, Mass.) is placed in a warm water bath. The bath overlays the anterior epicardial surface. The transducer is mounted on a clamp and lowered into the bath. It is adjusted until an optimal stable short axis view of the left and right ventricle has been obtained at the ventricular mid-papillary muscle level. These images are then be used to assess left ventricular cavity and myocardial uptake of contrast following intravenous injection.

EXAMPLE 1

Visually Apparent Consistent Myocardial Opacification with PESDA

Five open chest dogs were given incremental intravenous injections of perfluoropropane enhanced sonicated dextrose albumin (PESDA), produced as hereinbefore described, in doses of 0.02, 0.04, 0.06, 0.08 milliliter per kilogram (ml/kg). During intravenous injection, pulmonary artery pressure, left ventricular end-diastolic pressure, systolic pressure and cardiac output were monitored. Myocardial peak videointensity was measured using a 3.5 Megahertz epicardial transducer. Mean transit time of the contrast agent and half-time of contrast washout were also measured. Table 1 demonstrates that myocardial peak videointensity increased linearly with increasing dose of intravenous PESDA ($r=0.65$, $p<0.0001$).

TABLE 1

| Dose ml/kg | PAP | LVSP | CO | MPVI |
| --- | --- | --- | --- | --- |
| 0.02 | 21.3 ± 3.8 | 105 ± 11.3 | 2.4 ± 0.5 | 7.6 ± 6.8 |
| 0.04 | 23.3 ± 4.6 | 103.5 ± 9.5 | 3.1 ± 0.9 | 17.9 ± 9.8 |
| 0.06 | 24.1 ± 4.0 | 102.7 ± 8.5 | 3.0 ± 0.9 | 22.2 ± 10.9 |
| 0.08 | 28.0 ± 3.5 | 102.2 ± 8.7 | 2.9 ± 0.8 | 25.5 ± 10.7 |

PAP = pulmonary artery pressure; LVSP = left ventricular systolic pressure; CO = cardiac output; MPVI = myocardial peak videointensity;

Visible myocardial opacification was seen in 100% of the 0.04–0.08 ml.kg intravenous injections. Table 1 demonstrates that low doses of PESDA produce consistent, visual myocardial opacification following intravenous injection; the degree of myocardial opacification is linearly related to the dosage; and, PESDA causes minimal hemodynamic changes and has physiologic washout times. PESDA is, therefore, a novel contrast agent which can non-invasively detect myocardial perfusion.

EXAMPLE 2

Use of PESDA to Quantify Coronary Blood Flow

Six open chest dogs were given 0.06 milliliter per kilogram (ml/kg) intravenous injections of perfluoropropane-enhanced sonicated dextrose albumin (PESDA), prepared as hereinbefore described. A total of 45 intravenous injections of PESDA were given in the eight dogs. Myocardial peak videointensity was measured and quantified using a 3.5 Megahertz epicardial transducer connected to a commercially available ultrasound scanner (Hewlett Packard Company, Andover, Mass.). Coronary blood flow was measured using a Transonic Doppler Flow Probe placed around the proximal left anterior descending artery. Cardiac output was measured using thermodilution. Table 2 demonstrates that there is a significant correlation between myocardial peak videointensity and coronary blood flow.

TABLE 2

| Dog # | Dose | # consecutive IV injection | Average MPVI | Average CBF (cc) | Average CO (L) |
| --- | --- | --- | --- | --- | --- |
| 1 | 0.06 ml/kg | 3 | 13 | 17 | 1.9 |
| 2 | 0.06 ml/kg | 2 | 41 | 40 | 4.0 |
| 3 | 0.06 ml/kg | 2 | 34 | 28 | 2.9 |
| 4 | 0.06 ml/kg | 2 | 14 | 21 | 2.3 |
| 5 | 0.06 ml/kg | 2 | 29 | 21 | 3.1 |
| 6 | 0.06 ml/kg | 2 | 16 | 17 | 3.0 |

IV = intravenous; MPVI = myocardial peak videointensity; CBF = coronary blood flow; CO = cardiac output Visually evident myocardial opacification was seen with PESDA following all intravenous injections. Multiple linear regression analysis demonstrated that MPVI correlated closest with coronary blood flow and not cardiac output. The myocardial PVI produced by intravenous injections of PESDA correlates with coronary blood flow over a wide range of flows and pathophysiologic events. This new ultrasound contrast agent, therefore, may be utilized to non-invasively quantify coronary blood flow in a wide variety of coronary diseases.

EXAMPLE 3

Use of PESDA to Non-Invasively Assess Renal Perfusion

Five dogs were given 0.06 milliliter per kilogram (ml/kg) intravenous injections of perfluoropropane-enhanced sonicated dextrose albumin (PESDA), produced as hereinbefore described. A total of 26 intravenous injections were given. Renal imaging and qualitative contrast enhancement were performed during the intravenous injections using an external 4.5 Megahertz linear array transducer connected to a commercially available ultrasound scanner (Hewlett Packard Company, Andover, Mass.). Renal artery blood flow was monitored using a Transonic Doppler probe around the renal artery. Ultrasound enhancement was qualitatively graded as "0"=no enhancement, "1+"=mild, "2+"=marked enhancement. Renal artery stenosis was induced at certain periods to decrease renal artery blood flow to less than 10% of baseline in order to determine a correlation between contrast and renal artery blood flow.

TABLE 3

| Dog # | IV inject. dose | Average PRCV | Average RABF (ml) | Average PRCV following RAS | Qualitative enhancement |
| --- | --- | --- | --- | --- | --- |
| 1 | 0.06 ml/kg | n/a | n/a | n/a | 2+ |
| 2 | 0.06 ml/kg | 15 | n/a | n/a | 2+ |
| 3 | 0.06 ml/kg | 16 | 53 | n/a | 2+ |
| 4 | 0.06 ml/kg | 28 | 117 | 9 | 2+ |
| 5 | 0.06 ml/kg | 24 | 121 | 11 | 2+ |

IV = intravenous; PRCV = peak renal cortex videointensity; RABF = renal artery blood flow; RAS = renal artery stenosis; n/a = not available.

Following all 26 intravenous injections of PESDA, there was a 2+ contrast ultrasound enhancement of the renal cortex. The results in Table 3 demonstrate that renal artery and cortical blood flow abnormalities can be detected using intravenous PESDA. These results also demonstrate that PESDA can be utilized to non-invasively detect renal artery stenosis or other causes of abnormal renal perfusion.

EXAMPLE 4

Use of PESDA to Visually Identify Acute Myocardial Ischemia and Reperfusion

Six open-chest dogs were given 0.06 milliliter per kilogram (ml/kg) intravenous injections of perfluoropropane-enhanced sonicated dextrose albumin, produced as hereinbefore described. Injections were given at baseline, within fifteen (15) minutes of ligation of the proximal left anterior descending artery (LAD), and after the LAD blood flow was restored. Ischemia was attained by ligating the LAD with silk or umbilical suture. The artery was clamped for a variable time interval and then released. The duration of ischemia was 10 minutes to 160 minutes. LAD blood flow was continuously monitored with a Transonic Doppler flow cuff. Myocardial peak videointensity (MPVI) was determined following each intravenous PESDA injection. Table 4 demonstrates that quantitatively evident contrast was seen in the anterior myocardium at baseline.

TABLE 4

| Dog # | MPVI at Baseline | MPVI at Ligation | MPVI at Reperfusion |
|---|---|---|---|
| 1 | 18 | 1.7 | 33 |
| 2 | 16 | 2.0 | 36 |
| 3 | 14 | 1.0 | 40 |
| 4 | 40 | 1.0 | 62 |
| 5 | 14 | 3.7 | 40 |
| 6 | 29 | 3.0 | 45 |

MPVI = myocardial peak videointensity

Table 4 demonstrates that intravenous PESDA can identify acutely ischemic and reperfused myocardium non-invasively. This new agent significantly improves the ability to rapidly identify whether coronary patency has been achieved following mechanical or pharmacologic revascularization.

EXAMPLE 5

Use of Aminophylline to Enhance the Contrast Effects of PESDA

Six dogs were each given two equivalent quantities of two different samples of 0.08 milliliter per kilogram (ml/kg) intravenous injections of PESDA. One sample (PESDA-AM) was mixed with 2 milligrams (mg) of Aminophylline (AM) prior to sonication and another was sonicated without AM (PESDA). Myocardial peak videointensity was measured from the anterior myocardium using a 3.5 Megahertz epicardial transducer. Cardiac output was measured following each intravenous injection using thermodilution technique. Mean pulmonary and left ventricular systolic artery pressures were monitored during intravenous injection and coronary flow was measured using a Transonic Doppler flow cuff around the left anterior descending artery. Table 5 demonstrates the ability of this subtherapeutic dose of Aminophylline to enhance the contrast effects of PESDA.

TABLE 5

| | CO | LAD CF | LVS | MPA | MPVI |
|---|---|---|---|---|---|
| PESDA alone | 3.2 ± 0.8 (L/min) | 33 ± 13 ml | 103 ± 11 (mm Hg) | 24 ± 5 (mm Hg) | 21 ± 12 |
| PESDA - AM | 3.5 ± 1.0 (L/min) | 34 ± 18 ml | 104 ± 11 (mm Hg) | 24 ± 5 (mm Hg) | 30 ± 12* |

*$p<0.0001$ (paired t test)
CO = cardiac output; LAD CF = left anterior descending artery; LVS = left ventricular systolic pressure; MPA - mean pulmonary artery pressure; MPVI = myocardial peak videointensity; L/min. = liters per minute; mm Hg = millimeters of mercury; ml = milliliter.

EXAMPLE 6 (PROPHETIC)

Use of Perfluoropropane Enhanced Sonicated Dextrose Albumin to Determine Myocardial Blood Flow in Humans A 0.04–0.08 milliliter/kilogram injection of the sonicated dextrose albumin produced as described in Example 7, is given intravenously over 3–5 seconds followed by a 10 milliliter normal saline flush. (The dose range is patient-specific: large patients may require slightly higher doses to produce equivalent left ventricular contrast effects). All patients receive a 0.04 ml/kg dose as the initial injection. If this fails to produce myocardial opacification, a 0.08 ml/kg dose is then given. The dose which produces myocardial opacification and improved detection of abnormal wall motion and left ventricular ejection fraction is used to determine myocardial blood flow by contrast echocardiography performed using the standard technique described in Weyman, Arthur E., "Principles and Practice of Echocardiography", Lea & Febiger, Malvern, Pa. (1994, 2d Edition) and using the commercially available Hewlett Packard Sonos 1500 Phased Array Imaging System (Hewlett Packard, Andover, Mass.). Throughout the echocardiographic procedure, the patient's heart rate, blood pressure and oxygen saturation are monitored and recorded. The peak videointensity (corrected for baseline intensity) in the left ventricular cavity and myocardium for each injection is obtained.

For most ultrasound imaging, the contrast agent of this invention is formulated in a pharmaceutically effective dosage form for peripheral intravenous administration to the host to be imaged. Generally, such host is a human subject, although other mammalian hosts, such as canine or equine, can be imaged equally effectively. For preparation of the dosage forms of the contrast agents of this invention, generally, a sonicated mixture of commercially available albumin (human), USP, solution (generally supplied as 5% or a 25%, by weight, sterile aqueous solutions), and commercially available dextrose, USP, for intravenous administration are employed. This mixture is sonicated under ambient conditions, i.e., room air, temperature and pressure, and is perfused with perfluoropropane or other commercially available inert gas (99.9% by weight) during sonication.

Generally, USP dextrose is commercially available as 5% up to 70%, by weight, aqueous solutions; 5% dextrose, injection, USP being preferred. Upon peripheral venous administration of the contrast agent of this invention to a subject to determine myocardial blood flow and peak myocardial videointensity by echocardiography, optimization of myocardial uptake and left ventricular videointensity is attained.

The contrast agents of this invention can be produced by first preparing a solution of human serum albumin diluted with a dextrose solution. Thereafter, small and persistent echogenic contrast agent microbubbles are produced by sonicating the solution in room air with exposure to perfluoropropane during sonication. These bubbles appear to be the source of the echo contrast effect. Thus, the method employed for producing these bubbles must be capable of producing bubbles of sufficiently small size to pass through the microvasculature, yet large enough to permit effective echocardiographic visualization of the left ventricular myocardium and ultrasonic visualization of the liver and kidneys. Sonication by ultrasonic energy causes cavitation within the dextrose-albumin solution at sites of particulate matter or gas in the fluid. These cavitation sites eventually resonate and produce small microbubbles (about 4 to about 7 microns in size) which are non-collapsing and stable.

It has been demonstrated that a microbubble concentration of greater than $4 \times 10^8$/ml and microbubble size range of 5–6 microns are preferred for obtaining optimum left ventricular videointensity. However, the contrast agents of this invention, using a mixture containing suitable quantities of albumin and dextrose sonicated in the presence of perfluoropropane in accordance with the methods of this invention, produce the critical microbubble concentrations and enhanced myocardial uptake, which can be correlated with myocardial blood flow. Such concentrations are believed to be unique and critical to obtaining the equally unique echocardiographic properties demonstrated hereinafter. In general, and as discussed more fully hereinafter, sonication conditions which produce concentrations of greater than about 4×10⁸/ml of between about 5 and about 6 micron microbubbles are preferred.

During sonication, the solution is perfused with perfluoropropane, which has a lower gas diffusion coefficient and blood solubility than oxygen and nitrogen, to modify the internal gas composition of the microbubble. Perfusing the contrast agent with the gases of this invention during sonication, to produce more stable microbubbles, results in a significantly improved transpulmonary passage, myocardial uptake and left ventricular chamber uptake, when compared with a similar sample of sonicated albumin alone. This has three very important clinical implications. First, by improving myocardial and left ventricular uptake compared to sonicated albumin alone, the perfluoropropane-enhanced dextrose/albumin combination improves myocardial opacity and makes possible not only the qualitative echocardiographic detection of myocardial uptake and perfusion after an intravenous injection, but also enable echocardiographic quantification of myocardial perfusion. Such quantification is comparable to state of the art nuclear imaging, but without the need for radiation. Secondly, formulation with dextrose permits administration of the mixture by a non-invasive intravenous pathway. Thirdly, the use of dextrose solutions to dilute scarce and expensive human serum albumin, reduces contrast agent cost.

In one embodiment of this invention, a contrast agent is provided, consisting essentially of a sonicated mixture of about a two-fold to about a five-fold dilution of sterile human serum albumin, preferably a commercially available 5% by weight aqueous solution, with about 5% by weight aqueous dextrose, said contrast agent being in a pharmaceutically effective dosage form for intravenous injection.

In a preferred embodiment of this invention a multifold dilution of aqueous albumin with between about 5% and about 50% by weight of aqueous dextrose solution is employed. Excellent results have been achieved when the contrast agent is sonicated (in accordance with the procedures hereinafter described) for at least about 80 seconds and concomitantly exposed to perfluoropropane for at least about 5 seconds during sonication.

In another embodiment, the microbubbles of this invention are produced by sonication under conditions which optimize myocardial uptake and videointensity. In a preferred embodiment, the microbubbles are exposed to gaseous conditions which improve microbubble stability, decrease microbubble gas solubility and diffusibility in blood, and subsequently increase myocardial uptake. Consequently, highly preferred is an echocardiographic contrast agent comprising a sonicated mixture of between about a two-fold and about a five-fold dilution of human serum albumin with aqueous dextrose, exposed during sonication to a pharmaceutically acceptable gas of this invention.

In yet another embodiment, the sonicated microbubble solution is concentrated to enhance transpulmonary passage and myocardial uptake of the contrast agent. Consequently, highly preferred is an echocardiographic contrast agent in a pharmaceutically effective dosage form, enhanced with a pharmaceutically acceptable inert gas which lowers microbubble gas solubility and diffusivity in blood, and having a microbubble concentration of greater than about 5×10⁸/ml, capable of producing a peak myocardial videointensity which correlates quantitatively with coronary and myocardial blood flow.

Another embodiment of this invention relates to an improved method and composition for determining hepatic and renal perfusion using the ultrasound contrast agent of this invention.

As will be discussed hereinafter, in accordance with this invention, it has been found that an approximately two-fold to five-fold dilution of albumin with dextrose, sonicated under a room air atmosphere and perfused with a pharmaceutically acceptable inert gas, such as perfluoropropane, and administered intravenously, results in the best myocardial uptake and videointensity of any of the contrast agents investigated to date.

What is claimed is:

1. A pharmaceutically acceptable ultrasound contrast agent which relies on microbubbles for echogenicity, comprising:

microbubbles with an internal atmosphere enhanced with an amount of perfluoropropane gas which is effective for visually detecting myocardial contrast, said microbubbles formed from a solution of dextrose and albumin wherein said dextrose comprises about 3.75% by weight of said solution.

2. An ultrasound contrast agent comprising:

a sonicated aqueous albumin-dextrose solution wherein said dextrose comprises less than about 40% by weight of said solution and microbubbles with a perfluorocarbon gaseous content which is effective for visually detecting myocardial perfusion upon echocardiogram following peripheral intravenous injection of said agent into a host.

3. A method of ultrasonic imaging for use in medical procedures, comprising the steps of:

(a) injecting perfluoropropane-containing microbubbles in an albumin dextrose solution having less than 40% by weight of said solution comprising dextrose, into a mammal to thereby alter the acoustic properties of a predetermined area, and b) ultrasonically scanning an area including said predetermined area so as to obtain an image of said predetermined area.

4. A method of making an ultrasonic contrast agent for echocardiographic imaging comprising the steps of:

forming an aqueous protein solution containing 3.75% by weight of dextrose, and thereafter subjecting said solution to high frequency sonication while exposing said solution to perfluoropropane gas, said sonication forming stabilized microbubbles of relatively uniform size, containing said perfluoropropane, and capable of transpulmonary passage.

5. A method for myocardial, renal or heptic opacification comprising the following steps:

mixing human serum albumin with a solution comprising an aqueous monosaccharide in a ratio of 1:3 to 1:7 respectively to form a solution;

sonicating said solution for at least 80 seconds to form microbubbles approximately 3 to 5 microns in diameter, thereby forming an echo contrast agent;

intravenously injecting said solution into an animal subject; and detecting the image produced by ultrasound imaging.

6. The contrast agent of claim 2 wherein said mixture comprises between about a 2-fold to about an 8-fold dilution of said human serum albumin with about a 5% to about a 50% solution of aqueous dextrose.

7. The contrast agent of claim 2 wherein said mixture comprises about a 7-fold dilution of 50% dextrose.

8. The contrast agent of claim 2 wherein said mixture comprises about a 3-fold dilution of 5% dextrose.

* * * * *